United States Patent
Hamilton

(10) Patent No.: US 6,634,357 B1
(45) Date of Patent: Oct. 21, 2003

(54) RESUSCITATION VALVE ASSEMBLY

(75) Inventor: Robert M. Hamilton, Brea, CA (US)

(73) Assignee: Life Support Technology, Inc., Irvine, CA (US)

( * ) Notice: Subject to any disclaimer, the term of this patent is extended or adjusted under 35 U.S.C. 154(b) by 0 days.

(21) Appl. No.: 09/691,464

(22) Filed: Oct. 17, 2000

Related U.S. Application Data
(60) Provisional application No. 60/183,957, filed on Feb. 22, 2000.

(51) Int. Cl.$^7$ ................................................. A62B 9/02
(52) U.S. Cl. ............................... 128/205.24; 128/204.26
(58) Field of Search ................... 128/202.28, 202.29, 128/203.11, 204.26, 205.24, 207.12; 130/102

(56) References Cited

U.S. PATENT DOCUMENTS

| | | | | |
|---|---|---|---|---|
| 1,848,234 A | * | 3/1932 | Swope et al. | 128/205.24 |
| 2,418,034 A | | 3/1947 | Kizour | |
| 3,717,147 A | | 2/1973 | Flynn | |
| 3,726,274 A | * | 4/1973 | Bird et al. | 128/205.24 |
| 3,795,257 A | | 3/1974 | Fabish et al. | |
| 3,874,378 A | * | 4/1975 | Isaason et al. | 128/205.24 |
| 3,995,625 A | * | 12/1976 | Needham | 128/205.24 |
| 4,004,603 A | * | 1/1977 | Jones | 137/107 |
| 4,266,538 A | * | 5/1981 | Ruchti | 128/204.26 |
| 4,345,593 A | * | 8/1982 | Sullivan | 128/204.26 |
| 4,374,521 A | * | 2/1983 | Nelson et al. | 128/205.13 |
| 4,379,656 A | * | 4/1983 | Darling | 405/186 |
| 4,862,884 A | * | 9/1989 | Christianson | 128/204.26 |
| 4,898,174 A | | 2/1990 | Fangrow, Jr. | |
| 5,230,330 A | * | 7/1993 | Price | 128/203.11 |
| 5,357,951 A | * | 10/1994 | Ratner | 128/205.24 |
| 5,501,214 A | * | 3/1996 | Sabo | 128/205.24 |
| 5,575,279 A | * | 11/1996 | Beplate | 128/203.11 |
| 5,632,298 A | * | 5/1997 | Artinian | 137/102 |
| 5,722,394 A | * | 3/1998 | Loescher | 128/205.24 |
| 5,787,882 A | * | 8/1998 | Hamilton | 128/204.26 |
| 5,896,857 A | * | 4/1999 | Hely et al. | 128/205.24 |
| 6,055,981 A | * | 5/2000 | Laswick et al. | 128/204.18 |
| 6,189,532 B1 | * | 2/2001 | Hely et al. | 128/205.24 |

* cited by examiner

*Primary Examiner*—Weilun Lo
*Assistant Examiner*—Joseph F. Weiss, Jr.
(74) *Attorney, Agent, or Firm*—Harold L. Jackson

(57) ABSTRACT

A resuscitation valve assembly includes a housing with an inlet port adapted to be connected to a pressurized breathable gas source, such as oxygen, an outlet port adapted to be connected to a patient's airway and an ambient air port. The inhalation chamber is connected to the pressurized gas source when a manually operated valve, within the housing, is open and is disconnected from the inhalation chamber when the valve is closed. An inhalation/exhalation check valve is disposed between the inhalation chamber, the outlet port and the ambient air port to conduct the high pressure gas through the outlet port and into the patient's airway, vent the patient's exhaled gas through the ambient air port and allow ambient air to flow through the outlet port in response to the patient's spontaneous breathing.

17 Claims, 3 Drawing Sheets

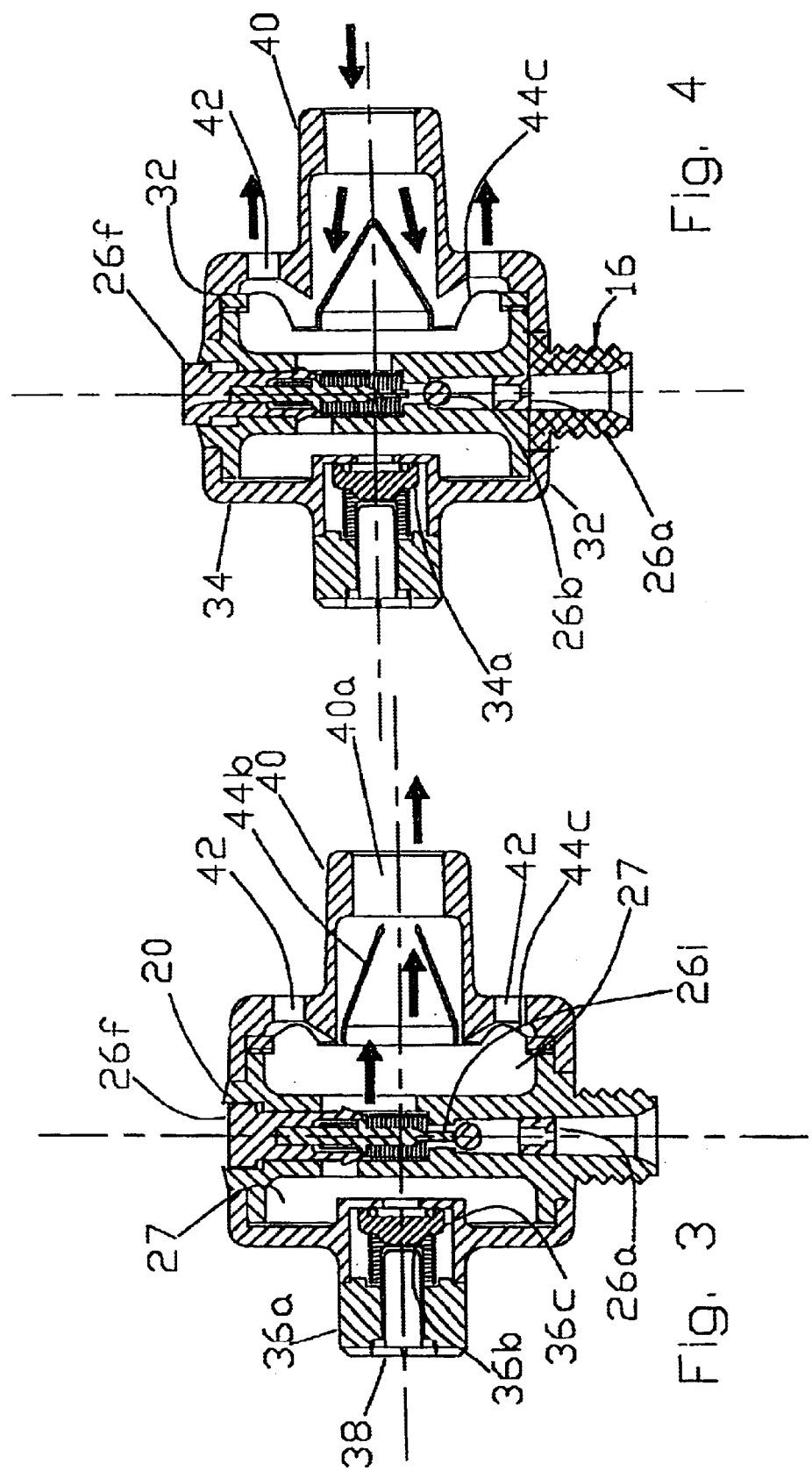

RESUSCITATION VALVE ASSEMBLY

RELATED APPLICATION

This is a complete application of provisional application serial No. 60/183,957 filed Feb. 22, 2000 entitled OXYGEN RESUSCITATION VALVE.

BACKGROUND OF THE INVENTION

1. Field of the Invention

The present invention relates to a resuscitation valve for supplying oxygen or an air/oxygen mixture to the airway of a patent or other individual as determined by an operator.

2. Description of the Prior Art

In instances of cardiac arrest or cessation of spontaneous breathing, emergency life support measures require a means to revive a patient's breathing function. This is most often accomplished by the use of a manually operated resuscitation device. These devices are powered by a high pressure oxygen or oxygen/air mixture source and administer the breathable gas either in response to the manually operable actuator device or in response to the commencement of the patient's natural breathing cycle when breathing is restored.

Such oxygen powered, manually operated demand valves are commonly used by emergency medical teams in the United States and other countries for resuscitating victims in heart and pulmonary distress. Such devices are typified by the arrangements described in U.S. Pat. No. 3,795,257, of which I am a co-inventor.

These devices contain many small and complex parts and are priced so as to make it impractical to consider them for single patient use (i.e., disposable devices). As a result it is necessary to sanitize these devices after each use and to routinely check and repair them.

The complexity of these prior art devices derives from their function as a demand valve, i.e., providing the patient with the oxygen or oxygen/air mixture frm the high pressure source when the breathing cycle is restored. In reality however, they are seldom used for this function. In the normal course of treatment, when spontaneous breathing is established, a simple continuous flow system is used to supply supplemental oxygen to the patient. Thus, the demand valve resuscitator is typically only used to establish spontaneous breathing.

There is a need for a simple and inexpensive device that will function to resuscitate the non-breathing patient according to "AHA" (American Heart Association) guidelines while accommodating a patient's spontaneous breathing.

SUMMARY OF THE INVENTION

A resuscitation valve assembly achieving the above goals includes a housing having an inlet port adapted to be connected to a patient's airway, an inhalation chamber within the housing, an outlet port and an ambient air port. A manually operated valve is mounted in the housing, e.g., within a centrally located tubular section which includes an axial bore in fluid communication with the inhalation chamber and terminating at one end at the inlet port. The valve preferably includes a plunger, which when manually depressed to a first position, dislodges a ball from an annular seat within the bore to connect the inhalation chamber to a source of pressurized oxygen or oxygen/air mixture. The plunger is normally retained in a second position, e.g., by means of a spring, to allow the gas from the high pressure source to force the ball against the annular seat and close the inlet port. The inhalation chamber is disconnected from the pressurized breathable gas source when the valve is in its second position.

An inhalation/exhalation check valve is disposed within the housing and adjacent the outlet and ambient air ports for allowing gas at above ambient air pressure within the inhalation chamber to pass through the outlet port and enter a patient's airway and for venting the individual's exhaled gas through the ambient air port. Means, which may comprise the inhalation/exhalation valve, functions in response to a sub-atmospheric pressure within the outlet port, due to the patient's spontaneous breathing, to allow ambient air to enter the patient's airway. The resuscitation valve preferably includes a pressure relief valve to set the maximum pressure within the inhalation chamber and an alarm responsive to an over pressure condition.

The resuscitation valve of my invention may comprise fewer than ten molded plastic parts and biasing means such as springs for the plunger and relief valve. The assembly is sufficiently simple and inexpensive to manufacture to be disposable after a single use thereby eliminating the time and considerable expense of sanitizing, testing and repairing required of the prior art devices.

BRIEF DESCRIPTION OF THE DRAWINGS

FIG. 3 is a cross-sectional view of the resuscitator valve assembly of FIG. 1, in an inhalation/nonspontaneous breathing mode, showing gas flowing from the pressurized source through the outlet (to the patient's airway);

FIG. 4 is a cross-sectional view of the resuscitator valve assembly in an exhalation mode with a patient's exhaled gas flowing back through the outlet to the atmosphere.

DESCRIPTION OF THE PREFERRED EMBODIMENT

Figure 1:
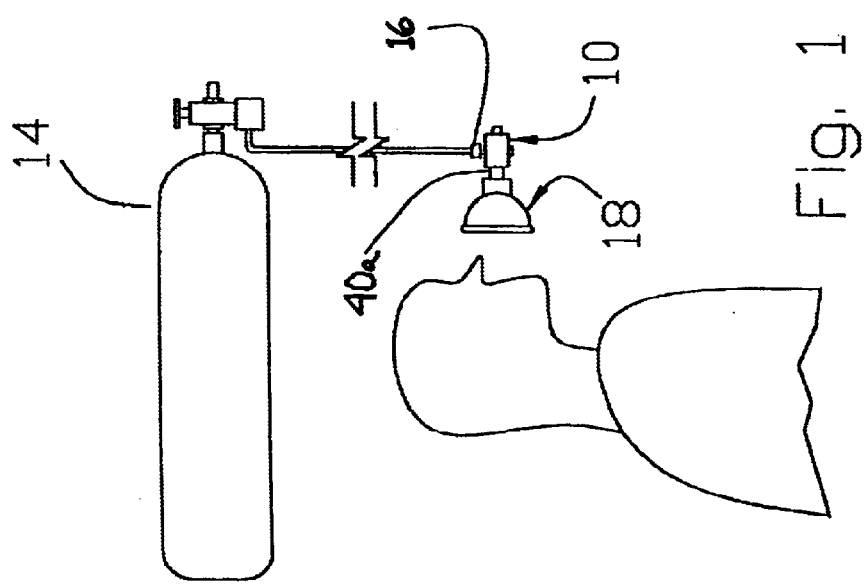
FIG. 1 is a diagrammatic view illustrating the use of a resuscitator valve assembly, in accordance with the present invention, when connected to a pressurized breathable gas source and a face mask.

Referring now to FIG. 1, a resuscitator valve assembly 10 has its inlet port 16 connected to a pressurized source of oxygen or an enriched air mixture 14 referred to herein as a breathable gas. An outlet 40a is connected to a face mask 18 which is adapted to be placed over a patient's nose and mouth to allow the oxygen or enriched air mixture to be forced into the patient's airway by an operator to ventilate the lungs and resuscitate the patient as will be explained in more detail.

Figure 2:
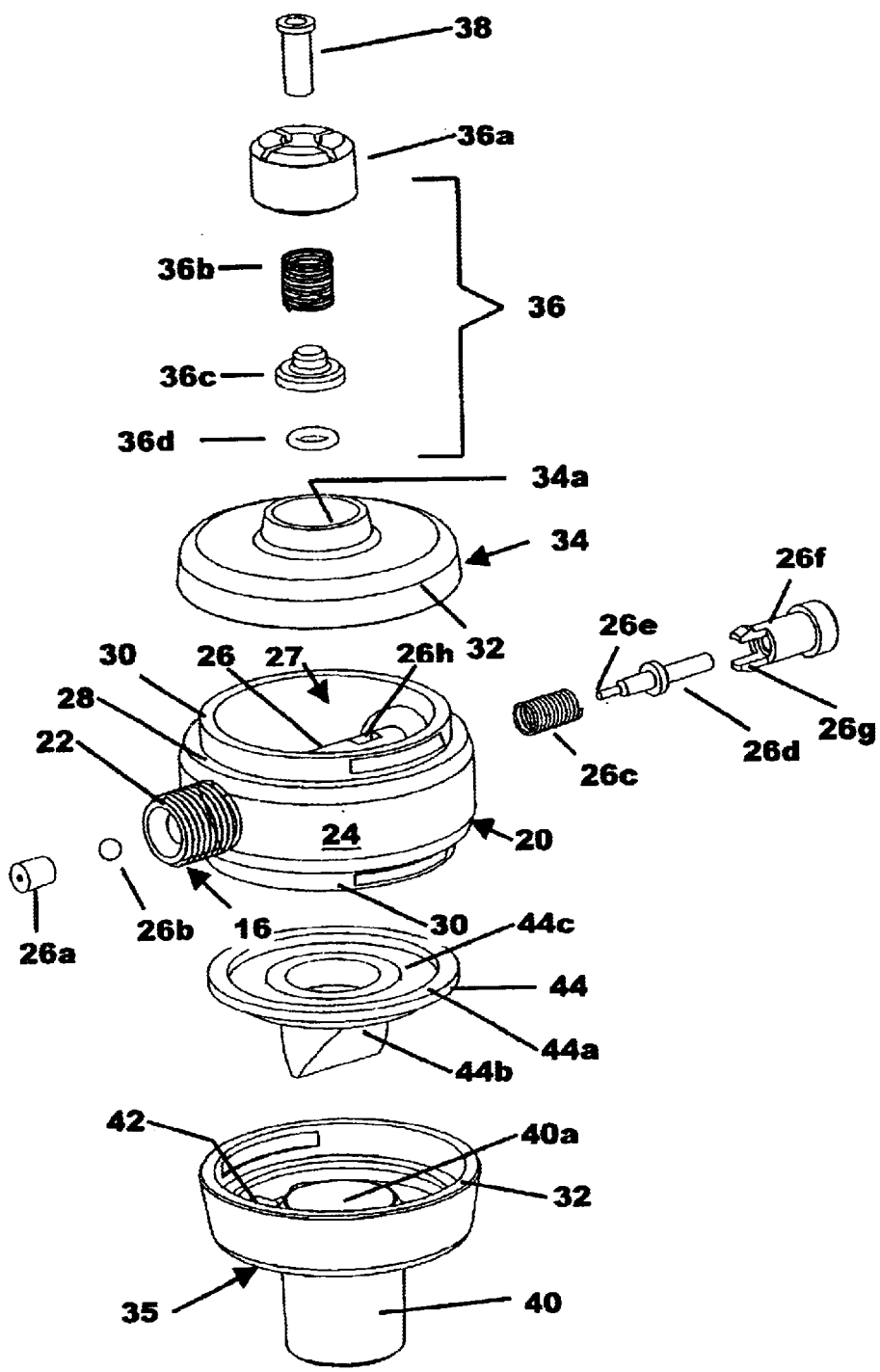
FIG. 2 is a perspective view of the resuscitator valve assembly, in a disassembled condition, showing the separate components thereof.

Referring now to FIGS. 2–4, a central cylindrically-shaped member 20 includes the inlet port 16 formed by an externally threaded nipple 22 on the peripheral wall 24. A tubular section 26 extends laterally across the central member and is formed, e.g., molded, integrally therewith. The tubular section houses a flow metering orifice 26a therein and a manually operable check valve including a ball 26b, bias spring 26c, and an actuating plunger consisting of rod 26d with a ball engaging finger 26e and an actuating button 26f with forwardly extending latching tongues 26g. The tubular section further includes openings 26h in the side wall thereof to allow breathable gas passing through the inlet port 16 to enter an inhalation chamber 27 surrounding the tubular section. The central member 20 further includes at each end an annular seat and protruding ring, 28 and 30, respectively, for mating with cooperating annular flanges 32, on the cover and outlet members 34 and 35 of the housing.

The cover member 34 is provided with an opening 34a in the top thereof for receiving a pressure relief valve 36 comprising a casing member 36a, a compression spring 36b, a pressure disk 36c and an O-ring 36d which provides a seal between the underside of the disk and a inwardly extending shoulder (to be described) of the cover member. An alarm element 38 is mounted in a centrally located opening in the casing 36a.

The outlet member 36 is provided with a tubular outlet extension 40 formed with an outlet passageway 40a and an ambient air port 42. A conventional duck inhalation/exhalation valve diaphragm 44 is positioned between the central and outlet members with an upper peripheral ring which is seated between the central and outlet members of the housing. The duck valve diaphragm is formed with a downwardly extending bifurcated flap 44b which opens and closes in response to a pressure differential as will be explained. The duck valve diaphragm further includes an annular flexible distal portion 42c which overlies the ambient air ports 42 to accommodate exhaled gas and inhaled air (in response to spontaneous breathing). The area of the duck valve diaphragm positioned over the outlet 40a is smaller than the area of the diaphragm exposed to the inhalation chamber as is illustrated in the. several figures. This results in an unbalanced valve. Thus, a negative pressure, i.e., lower than atmospheric, in the outlet 40a, will result in a negative pressure in the inhalation chamber, thereby causing the diaphragm to lift off of the ambient air ports 42 to allow ambient air to flow into the outlet.

The housing members as well as the other components, of FIG. 2, except for the springs, the duck valve and possibly the ball 26b are preferably made of an injection molded plastic such as polycarbonate. The simple construction of the resuscitator valve provides an inexpensive unit which is economically viable as a single use item, thereby eliminating the need to sanitize, test and repair the unit after use.

Figure 5:
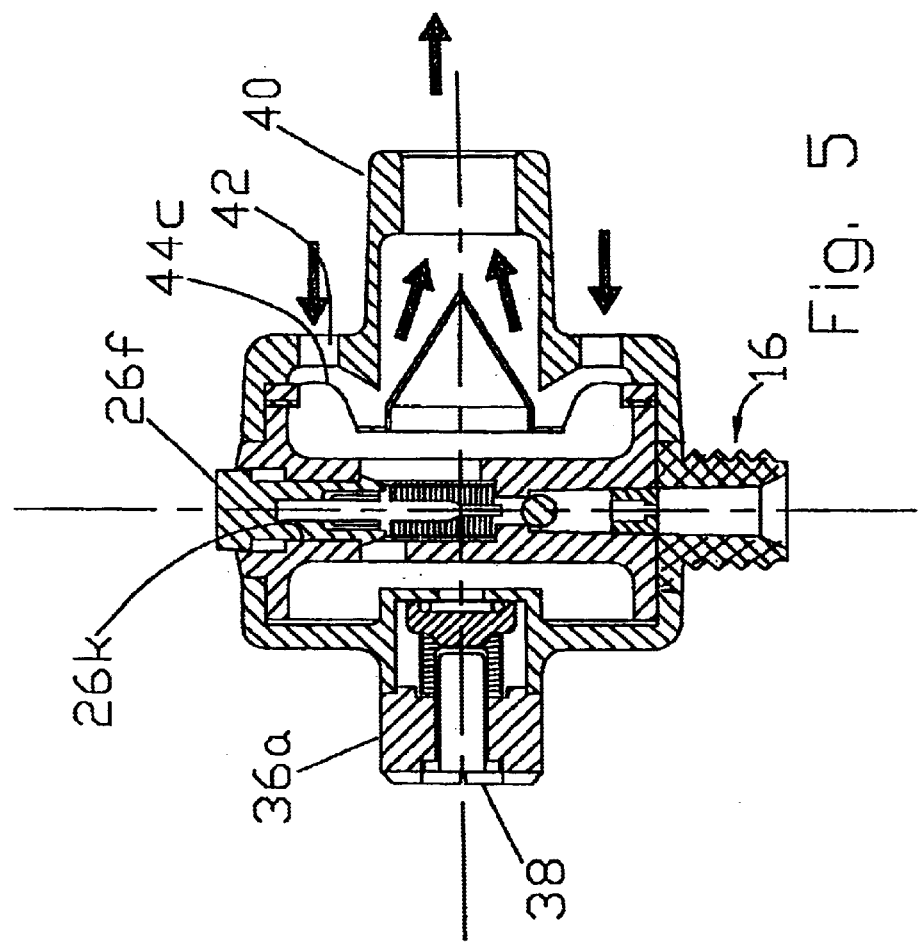
FIG. 5 is a cross-sectional view of the resuscitator valve assembly in an inhalation/spontaneous breathing mode with ambient air flowing into a patient's airway.

The operation of the resuscitator valve may best be understood by reference to FIGS. 3–5. FIG. 3 illustrates the resuscitation valve in an inhalation/nonspontaneous breathing mode in which the check valve 26b–f is open as a result of an operator pushing the plunger 26f inwardly to unseat the check valve ball from its seat 26j formed by an inwardly projecting shoulder on the inner wall of the central section 26 as illustrated in FIG. 3. Breathable gas from the container 14 passes through the metering orifice 26a, (which sets the flow rate), the passageway 26i in the interior of the central section downstream from the valve seat and thence into the inhalation chamber via the passageway 26h. The gas then flows through the open duck valve, the outlet opening 40a, the mask 18 and into the patient's airway via face mask 18. It should be noted that in this mode the annular portion 44c of the duck valve diaphragm 44 closes the ambient air ports 42.

FIG. 4 illustrates the resuscitator valve in its exhalation mode with the plunger 26e–f biased away from the inlet port by the spring 26c allowing the high pressure gas to close the check valve by forcing the ball 26b against its seat. The inner wall of 26k (FIG. 5) of the tubular section 26 preferably provides a sufficient clearance with the outer surface of the plunger to allow ambient air to pass into the inhalation chamber and return it to atmospheric pressure. In this mode the patient's exhaled air, which is above atmospheric pressure, closes the duck valve flap 44b and forces the disk 44c upwardly opening the ambient air ports 42 to vent the exhaled gas to atmosphere as is illustrated by the gas flow arrows in FIG. 4.

FIG. 5 illustrates the position of the valve components in the demand mode, i.e., when the spontaneous breathing has been restored. In this mode the sub-atmospheric pressure generated in the patient's airway creates a sub-atmospheric pressure in the inhalation chamber to cause the diaphragm to lift off of the ambient air ports 42 thereby allowing air to flow into the patient's lungs as is illustrated by the arrows. It should be noted that in the event that the inhalation chamber remains close to atmospheric pressure due to leakage around the stem of the plunger 26f the presence of a check valve (not shown) between the inhalation chamber and the atmosphere located, for example, in the cover member, a dual air path may result.

If desired a separate check valve may be provided in the central or cover members to allow ambient air to enter the inhalation chamber in lieu of depending on a clearance between the plunger and the inner wall of the section 26 to maintain the inhalation chamber substantially at atmospheric pressure when the check valve 26b–f is closed.

There has thus been described a novel resuscitation valve assembly which is simple and sufficiently inexpensive to be disposable after a single use. Modifications of the valve will be apparent to those skilled in the art without involving a departure from the spirit and scope of the invention as defined by the appended claims.

What is claimed is:

1. A resuscitation valve assembly apparatus comprising:
   a) a pressurized source of breathable gas;
   b) a valve housing having an inlet port connected to the pressurized breathable gas source, an outlet port adapted to be connected to an individual's airway, an inhalation chamber disposed between the inlet and outlet port and an ambient air port;
   c) a manually operated valve mounted in the housing for connecting the inhalation chamber to the inlet port to supply pressurized gas to the inhalation chamber in a first or open position, the inhalation chamber being disconnected from the inlet port when the manually operated valve is in a second or closed position regardless of the inhalation chamber pressure to prevent pressurized gas from entering the inhalation chamber; and
   d) an unbalanced inhalation/exhalation check valve disposed within the housing and adjacent the outlet and ambient air port for allowing fluid at above ambient air pressure within the inhalation chamber to pass through the outlet port and enter the individual's airway, for venting the individual's exhaled gas through the ambient air port, and for connecting the outlet port to atmosphere in response to a sub-atmospheric pressure within the outlet port to allow air to enter the individual's airway.

2. The resuscitation valve apparatus of claim 1 wherein the inhalation/exhalation check valve provides a passageway between the inhalation chamber and atmosphere when the source of pressurized gas is not connected to the inhalation chamber.

3. The resuscitation valve apparatus of claim 1 wherein the manually operated valve assembly comprises a check valve and a manually operable spring biased plunger.

4. The resuscitation valve apparatus of claim 3 wherein the housing includes a tubular section extending laterally across the housing defining an axial bore with a nipple at one end forming the inlet port, the spring biased plunger extending into the other end of the tubular section, the plunger having an axially extending actuating finger at one end thereof and a manually engageable knob at the other end, the tubular section defining an inwardly projecting shoulder forming an annular valve seat between the inlet port and the plunger, the check valve further including a ball disposed within the axial bore, the ball being forced against the seat when the pressure in the inlet port exceeds the pressure in the inhalation chamber, the spring biasing the actuating finger of the plunger away from the ball, the plunger being arranged to force the ball away from the seat in response to an axial force being applied to the knob in the direction of the inlet port, the tubular section further defining a fluid passageway between the axial bore and the inhalation chamber downstream from the valve seat.

5. The resuscitation valve apparatus of claim 4 further including a pressure relief valve disposed in the housing in fluid communication with the inhalation chamber for setting the maximum allowable gas pressure within the inhalation chamber.

6. The resuscitation valve apparatus of claim 5 further including an alarm disposed in the housing responsive to the pressure relief valve for providing an audible alarm when the pressure within the inhalation chamber exceeds the maximum allowable pressure.

7. The resuscitation valve apparatus of claim 6 wherein the housing is formed of three molded components comprising a disk-shaped cover member with the relief valve positioned therein, a cylindrically-shaped central section with the tubular section disposed therein, and a cup-shaped outlet member having the outlet port therein.

8. The resuscitation valve apparatus of claim 7 wherein the tubular section defines an inner wall surrounding the actuating plunger with a clearance there between to provide a passageway for ambient air to enter the inhalation chamber when the valve is in the closed position.

9. A resuscitation valve assembly apparatus comprising:
   a) a pressurized source of breathable gas;
   b) a valve housing having an inlet port connected to the pressurized breathable gas source, an outlet port adapted to be connected to an individual's airway, an ambient air port and an inhalation chamber disposed between the inlet and outlet port, the housing defining a fluid passageway between the inlet port and the inhalation chamber;
   c) a manually operated valve mounted within the passageway, the valve being arranged to connect the inhalation chamber to the inlet port to supply pressurized gas to the inhalation chamber in an open position and to disconnect the inhalation chamber from the inlet port when the manually operated valve is in a closed position whereby fluid cannot flow from the inlet port to the inhalation chamber when the manually operated valve is in a closed position regardless of the inhalation chamber pressure; and
   d) valve means disposed in the housing adjacent the outlet and ambient air ports for allowing fluid at above ambient air pressure within the inhalation chamber to pass through the outlet port and enter the individual's airway and for venting the individual's exhaled gas through the ambient air port, and for connecting the outlet port to atmosphere in response to a subatmospheric pressure within the outlet port to allow air to enter the individual's airway when spontaneous breathing commence.

10. The resuscitation valve apparatus of claim 9 wherein valve means comprises a passageway between the inhalation chamber and atmosphere when the source of pressurized gas is not connected to the inhalation chamber.

11. The resuscitation valve apparatus of claim 9 wherein the manually operated valve comprises a check valve and a manually operable spring biased plunger.

12. The resuscitation valve apparatus of claim 11 wherein the housing includes a cover member, an outlet member in which the outlet is disposed and a tubular section extending laterally there across defining an axial bore with a nipple at one end forming the inlet port, the spring biased plunger extending into the other end of the tubular section, the plunger having an axially extending actuating finger at one end thereof and a manually engageable knob at the other end, the tubular section defining an inwardly projecting shoulder forming an annular valve seat between the inlet port and the plunger, the check valve further including a ball disposed within the axial bore, the ball being forced against the seat when the pressure in the inlet port exceeds the pressure in the inhalation chamber, the spring biasing the actuating finger of the plunger away from the ball, the plunger being arranged to force the ball away from the seat in response to an axial force being applied to the knob in the direction of the inlet port, the tubular section further defining a fluid passageway between the axial bore and the inhalation chamber downstream from the valve seat.

13. The resuscitation valve apparatus of claim 12 further including a pressure relief valve disposed in the cover member in fluid communication with the inhalation chamber for setting the maximum allowable gas pressure within the inhalation chamber.

14. The resuscitation valve apparatus of claim 13 further including an alarm disposed in the cover member and responsive to the pressure relief valve for providing an audible alarm when the pressure within the inhalation chamber exceeds the maximum allowable pressure.

15. The resuscitation valve apparatus of claim 14 wherein the tubular section provides a fluid passageway between the inhalation chamber and the atmosphere when the manually operated valve is in the closed position.

16. The resuscitation valve assembly apparatus of claim 1 wherein the housing is formed of only three pieces namely (1) a cover member having a top wall with a pressure relief opening therein and an annular flange opposite the top wall, (2) a cylindrically shaped central member having a peripheral wall with an opening at one end of the wall defining the inlet port and forming a central section which defines the inhalation chamber with a cross-piece molded integrally with the central section and an annular seating ring being arranged to receive the annular flange of the cover member, the cross-piece defining an axial bore therethrough in fluid communication with the inlet port and a passageway connecting the axial bore to the inhalation chamber, and (3) a cup-shaped outlet member having an annular flange at one end for mating with the outer seating ring of the central member and defining a outlet port opposite the annular flange.

17. The invention of claim 16 wherein the three pieces are molded of a plastic material.

* * * * *